United States Patent [19]

Suglia et al.

[11] 4,376,113

[45] Mar. 8, 1983

[54] STABLE SUSPENSIONS AND POWDERS OF STABLE MICROCAPSULES AND THEIR PREPARATION

[75] Inventors: Jean-Claude Suglia, La Destrousse; Colette Meinard, Marseilles, both of France

[73] Assignee: Roussel Uclaf, Paris, France

[21] Appl. No.: 181,359

[22] Filed: Aug. 26, 1980

[30] Foreign Application Priority Data

Aug. 30, 1979 [FR] France .............................. 79 21743

[51] Int. Cl.³ ...................... A01N 25/28; A61K 9/34; A61K 9/50; B01J 13/02
[52] U.S. Cl. ................................ 424/34; 71/DIG. 1; 252/316; 424/35; 424/89; 424/93; 424/94; 424/186; 424/193
[58] Field of Search .......................... 252/316; 424/34

[56] References Cited

U.S. PATENT DOCUMENTS

| | | | |
|---|---|---|---|
| 3,336,155 | 8/1967 | Rowe ............................. | 252/316 X |
| 3,415,758 | 12/1968 | Powell et al. ...................... | 252/316 |
| 3,549,555 | 12/1970 | Hiestand et al. .................... | 252/316 |
| 3,565,559 | 2/1971 | Sato et al. ......................... | 252/316 X |
| 3,567,650 | 3/1971 | Bakan ............................... | 252/316 |
| 3,576,760 | 4/1971 | Gould et al. ....................... | 424/19 X |
| 4,056,610 | 11/1977 | Barber, Jr. et al. ................. | 424/32 |
| 4,082,688 | 4/1978 | Egawa et al. ....................... | 252/316 |

FOREIGN PATENT DOCUMENTS 931148 7/1963 United Kingdom ............... 252/316

Primary Examiner—Richard D. Lovering

Attorney, Agent, or Firm—Hammond & Littell, Weissenberger and Muserlian

[57] ABSTRACT

A process for the preparation of stable suspensions and powders of stable microcapsules containing at least one active material having a variable porosity comprising preparing a colloidal solution of equal parts by weight of gelatin and acacia gum with a total concentration of 4 to 6% by weight of the final emulsion, preparing an oil solution, suspension or emulsion of the active material at a concentration of 1 to 5% by weight of the final emulsion and containing a variable amount of organosoluble ethyl hydroxyethylcellulose, mixing the said two compositions with stirring at a temperature near 50° C. in the presence of an emulsifying agent to form an "oil in water" emulsion, effecting consecutively coacervation and microencapsulation of the emulsified droplets containing the active material by adjusting the pH to 4.2 to 4.4 by addition of an acid and then cooling the mixture to about 20° C. with stirring, reticulating the walls of the formed microcapsules by reaction with glutaric aldehyde and tannin with stirring at about 20° C. and either forming a concentrated suspension of microcapsules by slow addition at 20° C. of a water soluble ethyl hydroxyethylcellulose to the eticulated microcapsules or adding an antiagglomeration agent with stirring to the reticulated microcapsules at 20° C. and drying the resulting powder and the microcapsules produced thereby which are stable with respect to physico chemical influences and to exterior elements generally, such as sunlight and temperature changes so that the encapsulated active material maintains its activity.

25 Claims, No Drawings

STABLE SUSPENSIONS AND POWDERS OF STABLE MICROCAPSULES AND THEIR PREPARATION

STATE OF THE ART

Related processes are described in French Pat. No. 2,015,022 and No. 2,192,868 and Belgium Pat. No. 929,405.

OBJECTS OF THE INVENTION

It is an object of the invention to provide a novel process for forming microcapsules containing an active ingredient with a variable porosity.

It is another object of the invention to provide novel stable suspensions or powders of microcapsules containing an active ingredient protected against external conditions.

These and other objects and advantages of the invention will become obvious from the following detailed description.

THE INVENTION

The novel process of the invention for the preparation of stable suspensions and powders of stable microcapsules containing at least one active material, having a variable porosity comprises preparing a colloidal solution of equal parts by weight of gelatin and acacia gum with a total concentration of 4 to 6% by weight of the final emulsion, preparing an oil solution, suspension or emulsion of the active material at a concentration of 1 to 5% by weight of the final emulsion and containing a variable amount of organosoluble ethyl hydroxyethylcellulose, mixing the said two compositions with stirring at a temperature near 50° C. in the presence of an emulsifying agent to form an "oil in water" emulsion, effecting consecutively coacervation and microencapsulation of the emulsified droplets containing the active material by adjusting the pH to 4.2 to 4.4 by addition of an acid and then cooling the mixture to about 20° C. with stirring, reticulating the walls of the formed microcapsules by reaction with glutaric aldehyde and tannin with stirring at about 20° C. and either forming a concentrated suspension of microcapsules by slow addition at 20° C. of a water soluble ethyl hydroxyethylcellulose to the reticulated microcapsules or adding an antiagglomeration agent with stirring to the reticulated microcapsules at 20° C. and drying the resulting powder.

The microcapsules obtained by the process of the invention present a stability against physico chemical influences and more generally to exterior elements such as sunlight and temperature changes. It is useful to provide efficacy protection to microencapsulated active materials while keeping them biologically active.

The process of the invention permits one to obtain microcapsules with a variable porosity depending upon the need of utilization. In effect, thanks to the process, the porosity of the walls of the microcapsules can be controlled to meet the needs of the desired use.

The suspensions and powders which are also part of the invention and may be obtained starting from the microcapsules also present a remarkable stability during storage as well as a resistance to chemical influences and exterior elements such as light rays, changes in temperature and crushing resistance.

Procedures are known for the preparation of suspensions or powders in microcapsules containing an active material in an envelope obtained by coacervation of colloidal solutions and consecutive encapsulation of emulsified droplets such as in gelatin and acacia gum. According to these procedures, an aqueous colloidal solution of gelatin is prepared with heating and stirring and then an oil solution, suspension or dispersion of the active material is added thereto. The resulting emulsion is then subjected to coacervation and consecutive encapsulation of the active material present by adjustment of the pH by dilution with an acid or a base and cooling of the temperature of the reaction mixture.

Once the microcapsules are formed, one proceeds with the reticulation of the coacervate forming the walls of the envelope of the encapsulated droplets. The reticulation is effected either with an aldehyde or a derivative of the tannin family. The procedure will result in a suspension of the microcapsules obtained or the microcapsules may be isolated in the form of an powder.

The quality of the walls of the envelope forming the microcapsule is able to vary the degree of permeability which is a function of the porosity of the wall which depends upon various factors. Among the more determing factors are the rate and degree of cooling of the reaction medium temperature during coacervation, the amount of tannin used in the reticulation of the coacervate, the physical properties of the microencapsulated products such as viscosity, volatility and solid or liquid state, the thickness of the envelope wall or size of the products to be coated. For the same amount of product microencapsulated, the exchange surface was more important with microcapsules of small particles than of large particles.

By the execution of these processes, one is obliged to resort to very high rates of agitation to obtain microcapsules of a reasonably small size and this presents on the industrial scale a difficulty in the formation of foam during the agitation and of effecting other parts of the total installation. The total quantities of colloids used in the execution of these processes is very great and gives rise to the formation of microcapsules which is often not possible of the requisite quality. So, for example, the walls of the envelope formed become very dense which is impossible to effect correctly the reticulation of coacervate in depth. The resulting insolubility and resistance to exterior physical and chemical effects are not as good as desired.

This takes a great importance for the use of these microcapsules in agriculture, for instance. The duration of the life of the microcapsules containing the active matter, in this case, must be sufficient to ensure the maximum activity of the contained compound. On the other hand, the suspensions based on the microcapsules obtained by the processes can not be stored for prolonged periods, for example. In effect, often with these suspensions, one produces after a certain time a sedimentation of microcapsules and an agglomeration appears. When such a suspension is diluted for spraying, for example, there is a risk of non-homogenity and blockage of spray nozzles.

With respect to powders realized from the microcapsules of these processes, the microcapsules often tend to agglomerate and to stick when dried so that one is obliged in this case to resort to grinding to obtain a finely divided powder.

In contrast thereto, the process of the invention permits the obtention of microcapsules containing at least one active ingredient wherein the porosity of the walls can be controlled as needed. The microcapsules also have a surface stable to chemical influences and exterior elements and the suspensions and powders thereof are capable of being stored until ready for use.

The results obtained are due to the particular choice of parameters such as total concentration of colloids, the presence of agents to control the porosity, the rate of agitation, the choice of pH of the reaction medium, the ratio of the concentration of the colloids and the active materials to be encapsulated, the amount of organic solvent, the duration of coacervation by cooling the temperature and the choice of coacervation temperature and consecutive microencapsulation, the manner of effecting the reticulation of the coacervate in 2 steps and the manner of forming the suspensions and the powders from the microcapsules.

As the total concentration in colloids has a great incidence for the volume of coacervate to be obtained and as the microencapsulation is a superficial adsorption of the coacervate on the surface of the emulsified drops in the aqueous phase, at the perfecting of the present process, a particular attention is devoted to the choice of the colloid concentration with respect to the concentration of the active material and the amount of organic solvent.

By a judicious choice, the process of the invention permits the formation of a coacervate in an amount sufficient for coating the total surface of the droplets present in the "oil in water" emulsion with a layer of the desired quality. Among the desired quality of the layer of coacervate forming the wall of the microcapsule coating an emulsified droplet, the permeability plays on important role which permeability is a function of the porosity of the said wall proposed to be controlled by the process of the invention.

In effect, instead of determining on each occasion the numerous parameters governing a microencapsulation with an agent of gelatin and acacia gum to produce the walls of a determined porosity, as the prior art taught, it is advantageous to proceed in the following manner. During the first step, it is determined once for all the optimum parameters of one such microencapsulation as a function of the desired maximum porosity and with the parameters established, the process controls the wall porosity properly speaking. This purpose is attained by introducing into the emulsion destined for forming the coacervation a varying amount of a product capable to be occluded by the coacervate and the occlusion of the product provokes the closing of the pores of the wall formed by the coacervate. According to the quantity used of the product, the pores will be more or less closed and this will be able to control the porosity of the microcapsules.

It is not necessary to emphasize the importance of the porosity and its control in the case of microcapsules containing the active material. Due to this porosity, the active material can be diffused slowly or more rapidly depending on the order of the size of the pores of the wall and the nature of the said material. By knowing the desired time of the diffusion of an active material, one can produce microcapsules to provide a porosity which ensures this diffusion.

To satisfy the need of a resistance to chemical influences and more generally to exterior elements such as sunlight, temperature changes, solubility or mechanical resistance, the conditions of coacervation and of microencapsulation being determined can be found so this resistance is able to be notably improved if the reticulation of the coacervate is effected in 2 steps.

In effect, in the first stage of reacting the coacervate with an aldehyde, the latter is reacted with a part of the amine group of the gelatin and insolubilizes the formed microcapsules. In the second stage, the reticulation is completed by reaction with tannin which reacts with still free amine functions of the gelatin. In this manner, the transversal bonds between the gelatin molecules are established equally and a microcapsule acquires the desired qualities of stability.

The microcapsules obtained by the process of the invention can contain as the encapsulated products diverse pesticidal agents such as biocides, fungicides, insecticides, herbicides, acaricides, nematocides as well as viruses, enzymes, pheromones, juvenile hormones as well as attractive and artificial nutritive mediums. The said microcapsules may contain only one of the said agents or a plurality of them in association such as an insecticide associated with a pheromone, a juvenile hormone or a virus.

It is evident that the two or more agents in the same microcapsule must be chemically compatible and when this is not the case, the active materials are separately microencapsulated and they are ultimately admixed together.

The microcapsules of the invention are generally used in agriculture but may be used in other fields such as in paints and paper pulp to improve the persistence of action of the active principle or also in aerosols to avoid in the spraying too great an adsorption of the product by the support.

Among the possible utilizations, one can cite more precisely biological contest (for example, simulation of artificial eggs for production of trichograms), the formulation for progressive effects, possible preparations for attractants or repulsing agents over a prolonged period of time, treatment of wide area (ponds, forests), treatment of stables, microencapsulation of aqueous products and microencapsulation of incompatible active materials. It is equally of interest to combine microcapsules which do not contain an association such as combining microcapsules containing a pesticide such as a pyrethrinoid and microcapsules containing a pheromone, a juvenile hormone or a virus.

In the case of a utilization with an insecticide, the microcapsules of the invention may be conceived to either free the active ingredient into the atmosphere or to be ingested by insects to liberate the active ingredient in the interior of the insect body.

In preferred embodiments of the process of the invention, the "oil in water" emulsion is formed by agitation in the presence of an antifoaming agent at 400 to 600 rpm such as a secondary alcohol such as secondary octyl alcohol at a concentration of 0.2 to 0.7% by weight of the said emulsion and in the presence of a mixture of an anionic surface active agent and a non-ionic surface active agent, the concentration of the organosoluble ethyl hydroxyethylcellulose is 0.01 to 20% by weight of the colloids, the concentrations of the glutaric aldehyde is 2 to 5% by weight and the concentration of tannin is 3 to 8% by weight of the colloids and the rate of agitation is about 400 to 600 rpm at 20° C., 0.5 to 2% by weight of water-soluble ethyl hydroxycellulose is added to the suspension of reticulated microcapsules, 1 to 15% by weight of calcium chloride is added to the suspension of reticulated microcapsules, the calcium chloride and the water-soluble ethyl hydroxycellulose being added in the presence of a nonionic surface active agent while stirring at 400 to 600 rpm at 20° C., the antiagglomeration agent with which the reticulated microcapsules are treated is talc at a concentration of 7 to 13% by weight of the suspension containing the microcapsules.

Examples of preferred active materials to be microencapsulated are pyrethrinoid derivatives such as (S)α-cyano-3-phenoxy-benzyl (1R,cis) 2,2-dimethyl-3-(2,2-dibromovinyl)-cyclopropane-1-carboxylate or decamethrine and 5-benzyl-3-furyl-methyl (1R, 3S, E) 2,2-dimethyl-3-(2-oxo-2,3,4,5-tetrahydro-3-thiophenylidenemethyl)-cyclopropane-1-carboxylate or kadethrine, viruses such as Bacillus Thurigiensis and Heliothis Nuclear Polyhedrosis virus, an artificial nutritive medium an enzyme, a pheromone, a juvenile hormone, a non-pyrethrinoid insecticide, a herbicide, a biocide, a fungicide, an acaricide, a nematocide or an association of two or more of the said agents.

The stable suspensions and powders of the stable microcapsules containing the active ingredient are also part of the invention, especially stable suspensions or powders of microcapsules of active material such as pyrethinoid derivatives such as decamethrine or kadethrine, stable suspensions or powders of microcapsules containing a virus such as Bacillus Thurigiensis or Heliothis Nuclear Polyhedrosis virus and stable suspensions or powders of microcapsules containing an artificial nutritive medium, an enzyme, a pheromone a juvenile hormone, a non-pyrethrinoid insecticide, a herbicide, a biocide, a fungicide, an acaricide, a nematocide or an association of two or more of the said agents.

In a preferred embodiment of the process of the invention, the total concentration of colloids is selected so that it is preferably 5% to give under the selected conditions the maximum volume of coacervate, the active material is a water-insoluble liquid or solid and is in solution, suspension or emulsion in an organic solvent such as xylene, dimethyl phthalate or other phthalates. Such a solution, suspension or emulsion is prepared using a non-ionic surface active agent such as Galoryl EM 60 and an anionic surface active agent such as Galoryl 520 with the nature of the surface active agents as well as their concentration being selected so as not to affect the coacervation and microencapsulation. The acid used to adjust the pH is preferably 10% acetic acid.

During the preparation of a concentrated suspension, factors such as protection against gel formation, viscosity of the suspension and keeping the suspension during dilution have to be taken into account to obtain the desired microcapsules. For example, a 12% concentration of calcium chloride is used as an antigel agent. The choice of the thickening agent to adjust the viscosity of the suspension depends on the chemical inertia-against different constituents of a suspension. In the present case, water-soluble ethyl hydroxycellulose is used and the concentration of calcium chloride selected is that which avoids the appearance of flocculation of the ethyl hydroxyethylcellulose.

In preparing the powders of the microcapsules of the invention, talc at a concentration of about 10% by weight is added with stirring to the reaction mixture once accomplished the reticulation of the coacervate and the talc enrobes the reticulated microcapsules and prevents as well agglomeration during drying. In this manner, one avoids the need to grind agglomerated microcapsules to obtain a fine powder and the avoidance of grinding is an important advantage of the process of the invention so that there is no risk of damaging the walls of the microcapsules and there is no risk of modifying or changing the rate of diffusion of the desired active material.

In the following examples there are described several preferred embodiments to illustrate the invention. However, it should be understood that the invention is not intended to be limited to the specific embodiments.

EXAMPLE 1

An aqueous suspension of microcapsules with a low porosity containing (s)α-cyano-3-phenoxy-benzyl 1R,cis 2,2-dimethyl-3-(2,2-dibromovinyl)-cyclopropane-1-carboxylate (product A) or decamethrine were prepared as follows:

A first solution I was prepared by mixing at 500 rpm at 50° C. a mixture of 20 g of gelatin, 20 g of acacia gum, 760 ml of demineralized water and 0.5 g of sec.-octanol. A second solution II was prepared by stirring at 500 rpm at 50° C. a mixture of 25 g of compound A, 46.4 g of xylene, 96.6 g of dimethyl phthalate, 4.0 g of sec-octanol, 6.5 g of organosoluble ethyl hydroxyethylcellulose, 0.8 g of Galoryl EM 520 and 0.2 g of Galoryl EM 60.

An oil in water emulsion was formed by slowly introducing solution II into solution I while stirring at 500 rpm at 50° C. When the oil in water emulsion was formed, the pH of the reaction medium was adjusted to 4.2 to 4.4 by addition of 10% aqueous acetic acid solution and the temperature was then slowly lowered over one hour to 20° C. Then, 5 ml of 25% glutaric aldehyde were added thereto while stirring at 500 rpms. and after stirring the mixture at 500 rpms for one hour, 10 g of an aqueous 15% tannin solution were added thereto. The reaction mixture was stirred at 500 rpms at room temperature for about 3 hours to obtain reticulated microcapsules with a diameter not greater than 30 microns.

When the reticulated microcapsules were formed, 1 g of sec.-octanol, 119 g of calcium chloride added in small fraction, 10 g of water soluble ethyl hydroxyethylcellulose, 12 g of Galoryl EM 42 and 0.04 g of Rhodamine B were successively added thereto and the stirring was continued for about 3 hours. The resulting suspension passed through a screen to obtain a suspension containing 98.1% of the starting active principle.

EXAMPLE 2

An aqueous suspension of microcapsules with a high degree of porosity containing compound A was prepared by the procedure of Example 1 using the same amounts of reactants except that the organosoluble ethyl hydroxyethylcellulose was omitted from solution II to obtain a suspension of microcapsules with a great porosity containing 98.7% of the starting active ingredient.

EXAMPLE 3

The microcapsules of Examples 1 and 2 were isolated in the form of a powder by stirring the reaction mixture obtained in Examples 1 or 2 after reticulation of the coacervate at 500 rpms with 110 g of talc and the mixture was then stirred for about 15 minutes. The resulting suspension was then passed through a screen and was then vacuum filtered. The recovered microcapsules were dried to obtain a powder which would be conditioned by known methods, for example, in the form of baits.

EXAMPLE 4

A powder based on microcapsules containing a Heliothis Nuclear Polyhedrosis virus was prepared by stirring a first solution I at 500 rpms at 50° C. of 20 g of gelatin and 20 g of acacia gum and 760 ml of demineralized water. A second solution II was prepared by stirring a mixture of 25 g of a powder of Heliothis Nuclear Polyhedrosis virus, 46.4 g of xylene, 96.6 g of dimethyl phthalate, 0.8 g of Galoryl EM 520 and 0.2 g of Galoryl EM 60 at 500 rpms at 50° C.

An oil in water emulsion was formed by slowly adding solution II to solution I while stirring at 500 rpms at 50° C. When the oil in water emulsion was formed, the pH of the reaction mixture was adjusted to 4.2 to 4.4 by addition of aqueous 10% acetic acid solution and the mixture was slowly cooled over one hour to 20° C. 5 ml of 25% glutaric aldehyde were added with stirring at 500 rpms to the reaction mixture and after stirring at 500 rpms for one hour, 10 g of aqueous 15% tannin were added thereto with stirring. The mixture was stirred at 500 rpms at room temperature for about 3 hours to obtain reticulated microcapsules with a diameter not greater than 30 microns.

When the reticulated microcapsules were formed, 110 g of talc were added with stirring at 500 rpms to the reaction mixture obtained after reticulation of the coacervate and the mixture was stirred for about 15 minutes. The mixture was then passed through a screen and was vacuum filtered. The recovered microcapsules were dried to obtain a powder which could be conditioned by known methods such as formed into baits. It is noticeable that the process of the invention permits the microencapsulation of virus without exterminating them.

EXAMPLE 5

The porosity of the microcapsules prepared by the procedure of Examples 1 and 2 was studied while choosing as the microcapsuled material naphthalene in place of compound A. The concentration of the organosoluble ethyl hydroxyethylcellulose in solution I was varied in the tests as indicated in Table I.

TABLE I

|  | Test A | Test B | Test C |
| --- | --- | --- | --- |
| Naphthalene | 25% | 25% | 25% |
| Xylene | 75% | 70% | 65% |
| Organosoluble ethyl hydroxycellulose | 0 | 5% | 10% |

100 mg of microcapsules containing naphthalene formed in tests A,B and C were deposited on filter paper disks and as a reference, an equivalent amount of naphthalene not microencapsulized was placed on filter paper disks. The study was effected in the dark at a temperature of 25° C. and a 60% average relative humidity with a current of 143 m³/hour of air. The amount of naphthalene sublimated was determined by a vapor phase chromatographic apparatus after 24 hours, 7 and 28 days. The non-microencapsulated naphthalene was totally sublimated after 24 hours while the microcapsules of tests A,B and C showed the following percentages of loss of naphthalene as a function of time and amount of organosoluble ethyl hydroxyethylcellulose (EHEC) contained in the microcapsules shells.

TABLE II

|  | % sublimation | | |
| --- | --- | --- | --- |
|  | 24 Hours | 7 days | 28 days |
| non-microencapsulated Naphthalene | 100 | — | — |
| 0% EHEC microcapsules | 22 | 28 | 30 |
| 5% EHEC microcapsules | 16 | 22 | 24 |
| 10% EHEC microcapsules | 0 | 0 | 0 |

The results of the tests show the difference in porosity of the microcapsules depends upon the concentration of organosoluble ethyl hydroxyethylcellulose in the walls. By varying the concentration of organosoluble ethyl hydroxyethylcellulose in the microcapsules, it is possible to control the porosity of microcapsule walls as a function of the nature of the encapsulated active material and the destined usage.

EXAMPLE 6

The study of protection against light rays furnished to active material in the microcapsules of the invention was effected using as photosensitive compounds 5-benzyl3-furyl-methyl (1R, 3S, E) 2,2-dimethyl-3-(2-oxo-2,3,4,5-tetrahydro-3-thiophenylidenemethyl)-cyclopropane-1-carboxylate or kadethrine (compound B) in the microcapsules and suspension of microcapsules of the invention. The suspension and an emulsifiable concentrate based on the photosensitive compound at the same concentration were exposed to light rays similar to the solar spectrum at 25° C. and 75% relative humidity. The amount of loss of active material (compound B) was determined after 24 hours, 7 and 14 days exposure to the light rays using a high pressure liquid phase chromatographic apparatus. The results are reported in Table III.

TABLE III

| % of loss of | Time | | |
| --- | --- | --- | --- |
|  | 24 Hours | 7 days | 14 days |
| emulsifiable concentrate | 100% | 100% | 100% |
| microcapsule suspension | 13% | 54% | 71% |

The results of Table III show the good degree of protection of the active material when microencapsulated by the method of the invention.

EXAMPLE 7

A study of the preservation of the biological activity of an active material microencapsulated by the method of the invention was determined with compound A (Decamethrine) in the form of microcapsules in a suspension thereof or prepared in the form of granules prepared from a powder of the microcapsules. The suspension and the granules were compared to an emulsifiable concentrate based on an identical concentration of product A.

The study of the biological activity of the suspension of microcapsules and the emulsifiable concentrate was determined with the Spodoptera Littoralis caterpillar. The suspension of microcapsules and the emulsifiable concentrate were diluted with water and the two dilutions containing product A were sprayed at a rate of 10 ml per 4 bean plants having 8 leaves and then 20 caterpillars in the fourth larvae stage were placed on each plant on days 0,3,5,7 and 14 after the spraying. Readings were taken 24 and 48 hours later to determine the number of dead insects and the results are reported in Table IV with an application of 10 g/hl of compound A.

TABLE IV

| | % Mortality with infestation on days | | | | | | | | | |
|---|---|---|---|---|---|---|---|---|---|---|
| | 0 | | 3 | | 5 | | 7 | | 14 | |
| | 24H | 48H | 24H | 48H | 24H | 48H | 24H | 48H | 24H | 48H |
| Flowable microcapsules | 95 | 100 | 90 | 90 | 75 | 80 | 65 | 70 | 30 | 45 |
| emulsifiable concentrate | 100 | 100 | 5 | 15 | 5 | 5 | 0 | 10 | 5 | 10 |

The results of Table IV show that the emulsifiable concentrate has a very clear loss of activity after the third day while the suspension of microcapsules has a certain activity after 14 days.

The biological activity of the active material encapsulated according to the invention was studied while taking baits in the form of granules obtained from microcapsules isolated or in the form of a powder and containing compound A as the active material. It was tested as follows: The granules were spread on the soil to protect the lettuces against attack by caterpillars (Spodoptera Littoralis). First, it was ascertained that product A was placed in the baits directly without microencapsulation whereby it is very rapidly degraded and quickly lost its biological activity. The treated plot contained 20 lettuce plants in the 2-3 leaf stage laid out in 4 rows. 20 caterpillars were placed on the ground and on the 19th day after contamination, the number of dead and living caterpillars was determined and compared with the results obtained with a commercial product (Toxaphene). The results are reported in the following Table V.

TABLE V

| Compound | Dose in g/ha | Made of treatment | % of lettuce section | % of living caterpillars |
|---|---|---|---|---|
| A (microcapsules) | 500 | spreading on soil surface | 0 | 4% |
| Toxaphene (granules) | 100 | spreading on soil surface | 27.5 | 66.2 |

The results of the tests clearly demonstrate that with the process of the invention, it is possible to obtain stable suspensions or powders based on stable microcapsules containing active ingredients with assured control of the diffusion of the active ingredients depending on their nature and requirements of the use. It has been demonstrated that the microcapsules furnish for a material encapsulated a protection against chemical influences and exterior elements such as light rays and temperature changes while preserving the biological activity of the said material. The test data also shows that the results are useful for products normally used in the agricultural field.

However, all other active materials destined for alimentory, dietetic, diagnostic, pharmaceutical or parapharmaceutical use as well as all other active material for possible utilizations other than those mentioned previously are able to be microencapsulated by the process of the invention and the resulting microcapsules may be used in the usual manner.

Various modifications of the products and process of the invention may be made without departing from the spirit or scope thereof and it should be understood that the invention is intended to be limited only as defined in the appended claims.

What we claim is:

1. A process for the preparation of stable suspensions and powders of stable microcapsules containing at least one active material, having a variable porosity comprising preparing a colloidal solution of equal parts by weight of gelatin and acacia gum with a total concentration of 4 to 6% by weight of the final emulsion, preparing an oil solution, suspension or emulsion of the active material at a concentration of 1 to 5% by weight of the final emulsion and containing a variable amount of organosoluble ethyl hydroxyethylcellulose, mixing the said two compositions with stirring at a temperature near 50° C. in the presence of an emulsifyng agent to form an "oil in water" emulsion, effecting consecutively coacervation and microencapsulation of the emulsified droplets containing the active material by adjusting the pH to 4.2 to 4.4 by addition of an acid and then cooling the mixture to about 20° C. with stirring, reticulating the walls of the formed microcapsules by reaction with glutaric aldehyde and tannin with stirring at about 20° C. and either forming a concentrated suspension of microcapsules by slow addition at 20° C. of a water soluble ethyl hydroxyethylcellulose to the reticulated microcapsules or adding an antiagglomeration agent with stirring to the reticulated microcapsules at 20° C. and drying the resulting powder.

2. The process of claim 1 wherein the "oil in water" emulsion is formed by agitation at about 400 to 600 rpm in the presence of an antifoaming agent at a concentration of 0.2 to 0.7% by weight of the said emulsion and in the presence of a mixture of an anionic surface active agent and a non-ionic surface active agent.

3. The process of claim 1 wherein the concentration of the organosoluble ethyl hydroxyethylcellulose in the "oil in water" emulsion is 0.01 to 20% by weight of the colloids.

4. The process of claim 1 wherein the concentration of glutaric aldehyde is 2 to 5% and that of tannin is 3 to 8% by weight of the colloids and the stirring is about 400 to 600 rpm at 20° C.

5. The process of claim 1 wherein 0.5 to 2% by weight of water-soluble ethyl hydroxyethylcellulose is added to the suspension of reticulated microcapsules.

6. The process of claim 1 wherein 1 to 15% by weight of calcium chloride is added to the suspension of reticulated microcapsules.

7. The process of claim 1 wherein water-soluble ethyl hydroxyethylcellulose and calcium chloride were added with stirring at 400 to 600 rpm at 20° C. in the presence of a nonionic surface-active agent to the suspension of reticulated microcapsules.

8. The process of claim 1 wherein the suspension of reticulated microcapsules is treated with 7 to 13% by weight of talc as an antiagglomeration agent.

9. The process of claim 1 wherein the active ingredient to be microencapsulated is a pyrethrinoid derivative.

10. The process of claim 9 wherein the said derivative is (S)α-cyano-3-phenoxy-benzyl 1R, cis, 2,2-dimethyl-3-(2,2-dibromovinyl)-cyclopropane-1-carboxylate.

11. The process of claim 9 wherein the said derivative is 5-benzyl-3-furyl-methyl (1R,3S, E) 2,2-dimethyl-3-(2-oxo-2,3,4,5-tetrahydro-3-thiophenylidenemethyl)-cyclopropane-1-carboxylate.

12. The process of claim 1 wherein the active material to be microencapsulated is selected from the group consisting of virus, enzymes, pheromones and juvenile hormones.

13. The process of claim 12 wherein the active ingredient is a virus selected from the group consisting of Bacillus Thurigiensis and Heliothis Nuclear Polyhedrosis virus.

14. The process of claim 1 wherein the active material to be microencapsulated is an artificial nutritive media.

15. The process of claim 1 wherein the active material to be microencapsulated is selected from the group consisting of non-pyrethrinoid insecticides, herbicides, biocides, fungicides, acaricides and nematocides.

16. The process of claim 1 wherein the active material to be microencapsulated is a mixture of at least two materials selected from the group consisting of pyrethrinoid insecticides, virus, pheromones, enzymes, juvenile hormones, artificial nutritive medium, herbicides, biocides, non-pyrethrinoid insecticides, fungicides, acaricides and nematocides.

17. Stable suspensions or powders of stable microcapsules produced by the process of claim 1.

18. A suspension or powder of claim 17 wherein the microencapsulated active ingredient is a pyrethrinoid derivative.

19. A suspension or powder of claim 18 wherein the ingredient is (S)α-cyano-3-phenoxy-benzyl 1R, cis 2,2-dimethyl-3-(2,2-dibromovinyl)-cyclopropane-1-carboxylate.

20. A suspension or powder of claim 18 wherein the ingredient is 5-benzyl-3furyl-methyl (1R,3S,E) 2,2-dimethyl-3-(2-oxo-2,3,4,5-tetrahydro-3-thio-phenylidenemethyl)-cyclopropane-1-carboxylate.

21. A suspension or powder of claim 17 wherein the active material to be microencapsulated is selected from the group consisting of virus, enzymes, pheromones and juvenile hormones.

22. A suspension or powder of claim 21 wherein the active ingredient is a virus selected from the group consisting of Bacillus Thurigiensis and Heliothis Nuclear Polyhedrosis virus.

23. A suspension or powder of claim 17 wherein the active material to be microencapsulated is an artificial nutritive media.

24. A suspension or powder of claim 17 wherein the active material to be microencapsulated is selected from the group consisting of non-pyrethrinoids insecticides, herbicides, biocides, fungicides, acaricides and nematocides.

25. A suspension or powder of claim 17 wherein the active material to be microencapsulated is a mixture of at least two materials selected from the group consisting of pyrethrinoid insecticides, virus, pheromones, enzymes, juvenile hormones, artificial nutritive medium, herbicides, biocides, non-pyrethrinoid insecticides, fungicides, acaricides and nematocides.

* * * * *